(12) United States Patent
Tessier et al.

(10) Patent No.: US 6,476,194 B1
(45) Date of Patent: Nov. 5, 2002

(54) METHOD FOR FOLDING UNFOLDED PROTEINS

(75) Inventors: Daniel C. Tessier, Pierrefonds (CA); Andrë Zapun, Fontanil (FR); John J. M. Bergeron, Pointe Claire (CA); David Y. Thomas, Montreal West (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 09/342,106

(22) Filed: Jun. 29, 1999

(51) Int. Cl.[7] .............................. C07K 1/00; C07K 2/00; C12N 15/09
(52) U.S. Cl. ........................ 530/350; 530/300; 435/69.2
(58) Field of Search ................................. 530/350, 300; 435/69.2

(56) References Cited

U.S. PATENT DOCUMENTS 5,691,306 A * 11/1997 Bergeron et al. ............. 514/11

OTHER PUBLICATIONS

Zapun et al. J. Biol. Chem. 273: 6009–6012, Mar. 13, 1998.*
Kraehenbuhl et al. J. Cell Biol. 72: 406–423, 1977.*
Zapun et al. Mol. Biol. Cell 8: Suppl. pp. 97A, Nov., 1997.*
Glick DM. Glossary of Biochemistry and Molecular Biology, Revised Edition, Portland Press, London, p. 26, 1997.
Freedman, R. B., Hirst, T. R., and Tuite, M. F. (1994) *Trends Biochem Sci.* 19, 331–336.
Bergeron, J. J. M., Brenner, M. B., Thomas, D. Y., and Williams, D. B. (1994) *Trends Biochem Sci.* 19, 124–128.
Helenius, A., Trombetta, E. S., Hebert, D. N., and Simons, J. F. (1997) *Trends Cell Biol.* 7, 193–200.
Sousa, M., and Parodi, A. J. (1995) *EMBO J.* 14, 4196–4203.
Ou, W. J., Cameron, P. H., Thomas, D. Y., and Bergeron, J. J. M. (1993) *Nature* 364, 771–776.
Rodan, A. R., Simons, J. F., Trombetta, E. S., and Helenius, A. (1996) *EMBO J.* 15, 6921–6930.
Zapun, A., Petrescu, S. M., Rudd, P. M., Dwek, R. A., Thomas, D. Y., and Bergeron, J. J. M. (1997) *Cell* 88, 29–38.
Oliver, J. D., van der Wal, F. J., Bulleid, N. J., and High, S. (1997) Science 275, 86–88.
Elliott, J. G., Oliver, J. D., and High, S. (1997) J. Biol. Chem. 272, 13849–13855.
Darby, N. J., and Creighton, T. E. (1995) *Biochemistry* 34, 11725–11735.
Ou, W. J., Bergeron, J. J. M., Li, Y., Kang, C. Y., and Thomas, D. Y. (1995) *J. Biol. Chem.* 270, 18051–18059.
Hebert, D. N., Foellmer, B., and Helenius, A. (1996) *EMBO J.* 15, 2961–2968.
Kemmink, J., Darby, N. J., Dijkstra, K., Nilges, M., and Creighton, T. E. (1997) *Curr. Biol.* 7, 239–245.
Puig, A., and Gilbert, H. F. (1994) *J. Biol. Chem.* 269, 7764–7771.
Tatu, U., and Helenius, A. (1997) *J. Cell Biol.* 136, 555–565.

* cited by examiner

*Primary Examiner*—S. Devi
(74) *Attorney, Agent, or Firm*—France Cote; Christian Cawthorn; Swabey Ogilvy Renault (57) ABSTRACT

The present invention relates to methods of treating and diagnosing protein trafficking disorders and controlling secretory protein production. The present invention also relates to methods for folding unfolded proteins, especially in heterelogous expression systems. The methods comprise exposing an unfolded protein to a biological preparation comprising ERp57 in combination with calnexin or calreticulin under conditions to permit folding of the unfolded protein.

4 Claims, 3 Drawing Sheets

METHOD FOR FOLDING UNFOLDED PROTEINS

BACKGROUND OF THE INVENTION (a) Field of the Invention

The present invention relates to methods for detecting and treating protein trafficking disorders.

(b) Description of the Prior Art

The quality control system of the endoplasmic reticulum (ER) ensures that only folded proteins proceed further along the secretory pathway. Some of the abundant ER proteins are components of molecular chaperone systems which bind to unfolded proteins, retaining them in the ER. Enzymes which act to fold other proteins are also abundant in the ER and comprise several disulfide isomerases and prolyl peptidyl isomerases (Freedman et al., *Trends Biochem Sci.* 19:331–336 (1994)). How chaperones and folding enzymes interact to facilitate protein folding in the ER is not known.

Calnexin and calreticulin participate in a molecular chaperone system which integrates the processes of N-glycosylation and quality control (Bergeron et al., *Trends BioChem Sci.*, 19:124–128 (1994) and Helenius et al., *Trends Cell Biol.*, 7:193–200 (1997). They both are lectins that bind N-linked glycans of the form GlcNAc2Man9Glc1 which result from the removal of the two outer glucoses from a GlcNAc2Man9Glc3 oligosaccharide by the sequential action of glucosidases I and II. Removal of the innermost glucose by glucosidase II prevents binding by calnexin and calreticulin. Then, if the glycoprotein is unfolded, a glucose residue is added back to the high mannose core by the enzyme UDP–glucose:glycoprotein glucosyltransferase (UGGT) which recognizes unfolded proteins (Sousa et al., *EMBO J.*, 14:4196–420 (1995)3). Consequently, during folding glycoproteins undergo cycles of binding and release from calnexin and calreticulin which are driven by the addition and removal of a glucose residue (Helenius et al., *Trends Cell Biol.*, 7:193–200 (1997)). As a result of the specificity of UGGT, only unfolded glycoproteins bind to calnexin and calreticulin in vivo (Ou et al., *Nature,* 364:771–776 (1993) and Peterson et al., *Mol. Biol. Cell,* 6:1173–1184 (1995) ), even though these lectins do not recognize the conformation of their protein substrates (Rodan et al., *EMBO J.*, 15:6921–6930 (1996) and Zapun et al., *Cell,* 88:29–38 (1997)).

Monoglucosylated glycoproteins, in addition to binding to calnexin and calreticulin, can also apparently be crosslinked to the ER protein ERp57 (Oliver et al., *Science,* 275:86–88 (1997) and Elliott et al., *J. Biol. Chem.,* 272:13849–13855 (1997)) (also known as ER-60, ERp60, ERp61, GRP58, P58, HIP-70 or Q2; (Elliott et al., *J. Biol. Chem.,* 272:13849–13855 (1997). ERp57 is homologous to protein disulfide isomerase (PDI) and has been shown to exhibit thiol-disulfide oxidoreductase activity in vitro (Bourdi et al., *Arch. Biochem. Biophys.,* 323:397–403 (1995)).

Considering the impact of protein trafficking disorders and the lack of therapies to control protein trafficking disorders, it would be advantageous to be provided with methods to effectively diagnose and treat these disorders.

It would also be advantageous to be provided with methods for folding proteins into their biologically active correctly folded form.

SUMMARY OF THE INVENTION

It is an aim of the present invention to provide methods of treating and diagnosing protein trafficking disorders and controlling secretory protein production.

Another aim of the present invention is to provide methods for folding unfolded proteins, especially in heterologous expression systems.

In accordance with the present invention, there is provided methods for folding unfolded proteins or for enhancing the formation of folded proteins which comprise exposing an unfolded protein to a biological preparation comprising ERp57 in combination with calnexin or calreticulin under conditions to permit folding of the unfolded protein.

In accordance with the present invention, there is provided a kit for converting unfolded proteins to folded proteins or for enhancing the formation of folded proteins which comprises:

a) at least one of calnexin or calreticulin;

b) ERp57;

c) UDP-glucose:glycoprotein glucosyltransferase (UGGT);

d) the unfolded protein;

e) UDP-glucose; and f) an appropriate buffer.

The enzymes, calnexin and/or calreticulin can be fixed to a solid surface. For example, a carrier.

In accordance with the present invention, there is provided methods for forming disulfide bonds or for enhancing the formation of disulfide bonds in an unfolded protein which comprises the step of exposing an unfolded protein to a biological preparation comprising ERp57 in combination with calnexin or calreticulin under conditions to permit folding of the unfolded protein.

In accordance with the present invention, there is provided methods of increasing secretory protein production in a biological preparation, comprising administering an ERp57 suppressor agent to a biological preparation in an amount effective to increase secretory protein production.

In accordance with the present invention, there is provided agents which decrease ERp57 cooperation with calnexin or calreticulin for use in the manufacture of a medicament for increasing secretory protein production in a warm-blooded animal.

In accordance with the present invention, there is provided compositions which decrease ERp57 cooperation with calnexin or calreticulin for use in the manufacture of a medicament for treating a warmblooded animal for protein trafficking disorders which require reduction of ERp57 cooperation with calnexin or calreticulin.

In accordance with the present invention, there is provided compositions that include an agent which stimulates ERp57 cooperation with calnexin or calreticulin for use in the manufacture of a medicament for treating a warm-blooded animal for protein trafficking disorders which require stimulation of ERp57 cooperation with calnexin or calreticulin.

In accordance with the present invention, there is provided conjugates to the endoplasmic reticulum for use in the manufacture of a medicament for treating a warm-blooded animal for protein trafficking disorders.

In accordance with the present invention, there is provided methods of diagnosing a protein trafficking disorder in a warm-blooded animal, comprising the steps of:

a) exposing an anti-ERp57 antibody containing a reporter group to the ER of a warm-blooded animal under conditions and for a sufficient time to permit binding to ERp57;

b) detecting the amount of ERp57; and c) determining therefrom the presence of a protein trafficking disorder.

In accordance with the present invention, there is provided methods of diagnosing a protein trafficking disorder in a biological preparation, comprising the steps of:

a) exposing an anti-ERp57 antibody containing a reporter group to the biological preparation under conditions and for a sufficient time to permit binding to ERp57;

b) detecting the amount of ERp57; and c) determining therefrom the presence of a protein trafficking disorder.

DETAILED DESCRIPTION OF THE INVENTION

Prior to setting forth this invention, it may be helpful to first define certain terms that will be used herein.

"Protein trafficking disorder" refers to a disorder which affects secretory protein translocation, folding, or assembly in the ER. Representative examples of protein trafficking disorders include familial hypercholesterolaemia, cystic fibrosis, Tay-Sachs disease, congenital sucrose isomaltrase deficiency, and juvenile pulmonary emphysema.

"Secretory protein" refers to all N-linked glycosylated proteins and unfolded proteins processed through the ER, including all coagulation factors, all blood factors, all hormone and growth factor receptors and all ion channels including, by way of example, cystic fibrosis chloride channels and there are nicotinic and muscarinic acetylcholine receptors. Secretory proteins are membrane and luminal ER proteins which are N-glycosylated.

"Biological preparation" refers to any animal cell or tissue ex vivo. Suitable preparations include, by way of example, HepG2 cells, COS cells, 293 cells, and ATT20 cells.

"Molecular chaperone" refers to the class of proteins which stabilize unfolded or partially folded structures, prevent the formation of inappropriate intra- or interchain interactions, or interact with protein molecules to promote the rearrangement of protein-protein interactions in oligomeric structures.

"ERp57 cooperation with calnexin or calreticulin" refers to the association, including covalent and non-covalent binding, of ERp57 to calnexin or calreticulin.

"folded protein" means a secretory protein in its biologically active form.

"unfolded protein" means a secretory protein in a non-biologically active form.

The present invention provides methods for converting unfolded proteins into folded proteins. Proteins which can be converted include enzymes, growth factors (especially those with disulfide bonds), blood coagulation factors (e.g. Factor VIII), heterologous proteins produced at poor yield useful for therapeutic and diagnostic purposes (e.g. antibodies).

In a preferred embodiment, the unfolded proteins can be converted in vivo to folded protein by increasing the levels of ERp57 in cells which are producing heterologous proteins.

In a preferred embodiment, the unfolded proteins can be converted in vitro to folded protein by using optimum folding conditions and components as described in the present application.

The present invention provides methods and compositions directed to the regulation of secretory protein production, the diagnosis and the treatment of protein trafficking disorders.

Calnexin is a molecular chaperone which selectively associates in a transient fashion with newly synthesized monomeric glycoproteins and is thus active in the ER membrane. Calnexin associates with glycoproteins and incompletely folded secretory proteins. Dissociation of glycoproteins from calnexin occurs at different rates and is related to the time taken for their folding. This results in large differences and the rates of transport from the ER to the Golgi apparatus, with the rate limiting step governed by the time spent in the ER in association with calnexin.

The catalysis of disulfide bond rearrangement by ERp57 is more efficient on G1-glycoproteins in the presence of calnexin or calreticulin. This apparent specificity does not result from a direct recognition of the glycans by ERp57. As both the substrate and the enzyme are brought into close proximity by their respective interaction with the lectin, their relative local concentration is increased, resulting in the apparent enhancement of the catalytic activity.

In addition to the function of calnexin of retaining unfolded proteins in the ER, the affinity of calnexin for ERp57 serves to recruit this enzyme where it is needed. Disulfide bond formation and rearrangement, catalyzed by ERp57, can then occur while the glycoprotein is bound to calnexin. Therefore, the retention of unfolded proteins and the facilitation of their folding can be coordinated by calnexin and ERp57.

For proteins with multiple oligosaccharides such as influenza hemagglutinin, simultaneous binding to a multivalent calnexin may constrain the conformation of the protein so as to inhibit folding. Locking influenza hemagglutinin onto calnexin has been shown to inhibit the formation of disulfide bonds (Hebert et al. (1996) *EMBO J.*, 15:2961–2968). This class of glycoprotein may require at least partial release from calnexin, driyen by glucosidase II, to undergo folding and disulfide bond formation, which may then be catalyzed by ERp57.

Following cross-linking, ERp57 has been found in ternary complexes containing ERp57, a substrate protein and either calnexin or calreticulin (Elliott et al. (1997) *J. Biol. Chem.*, 272–13849–13855), but the present finding shows that they are convected through calnexin or calreticulin and that ERp57 does not bind glycoproteins directly.

The functional interaction between ERp57 and calnexin or calreticulin demonstrates that N-glycosylation does not only contribute to quality control but also to accelerate productive folding.

This study also suggests that other overlooked or difficult to detect interactions may add functionality to the other members of the PDI-family. Different proteins chaperone in the ER may have an associated member of the PDI family.

As noted above, one aspect of the present invention concerns increasing production of secretory proteins in either a biological preparation or a warm-blooded animal. As disclosed in the present invention, increase in the release of secretory proteins from the ER can be controlled by regulation of ERp57 cooperation with calnexin or calreticulin.

Any one of several techniques may be used to detect ERp57 cooperation with calnexin or calreticulin including those described in detail in Harlow, *Antibodies: A Laboratory Manual*, Cold Spring Harbor Laboratory (1988), incorporated herein by reference. By way of example, suitable methods include immunoprecipitation, followed by peptide mapping and protein sequencing. Briefly, this entails pulse-chasing cells and then immunoprecipitating, employing antibody. Anti-ERp57, anti-calnexin, or anti-calreticulin antibodies can be identified using any one of several techniques known in the art, e.g. those described in Harlow.

Confirmation of specific interaction may be subsequently accomplished by dissociation of the coimmunoprecipitate with SDS and reprecipitation with secretory protein specific antibody. This technique is described in detail in Harlow, *Antibodies: A Laboratory Manual*, Cold Spring Harbor Laboratory (1988). However, when employing this technique, it is important to use the appropriate detergent in precipitation. Suitable detergents include, by way of example, cholate, deoxycholate, digitonin and CHAPS to preserve the interaction, strong detergents, such as SDS tend to destroy the interaction.

ERp57 cooperation with calnexin or calreticulin may also be demonstrated or detected by cross-linking with bifunctional agents. This technique is especially for those interested in MHC1 and T-cell receptors and is described in detail in Ahluwalia, *J. Biol. Chem.* 267:10914–10918 (1992); Degen, *J. Cell. Biol.*, 112:1099–1115 (1991); Hochstenbach, *Proc. Natl. Acad. Sci. USA*, 89:4734–4738 (1992); and Galvin, *Proc. Natl. Acad. Sci. USA*, 89:8452–8456 (1992).

ERp57 cooperation with calnexin or calreticulin may also be demonstrated or detected using in vitro transcription and translation of cDNAs with translocation into microsomal vesicles to experimentally examine associated proteins with the endogenous calnexin, calreticulin or ERp57 present in these vesicles. This technique can be used to easily monitor secretory proteins for their potential to associate with calnexin.

Secretory proteins in transient association (i.e., those which are released after folding) with calnexin and/or calreticulin include, by way of example, α1-antitrypsin, α1-antichymotrypsin, transferrin, apoβ-100, complement 3 (C3), gp80 human complement-associated protein, and α-fetoprotein.

Secretory proteins retained, i.e. delaying their release into the luminal pathway, by calnexin and/or calreticulin in the ER include the unassembled T-cell receptor subunits, acetylcholine receptor subunits, HMG CoA reductase, murine class 1 histocompatibility protein (MHC1) (prior to association with β2 microglobulin), and H2a subunit of asialoglycoprotein receptor and any mutant or misfolded glycoproteins. Misfolded or mutant glycoproteins are retained by calnexin and are ultimately degraded by ER resident proteases or transported to lysosomes for degradation.

Suppression of ERp57 cooperation with calnexin or calreticulin increases the rate or release of secretory proteins. Secretory proteins in transient association with calnexin are translocated through the membrane more quickly. Those which would ordinarily be retained by calnexin are released directly through the luminal pathway.

ERp57 cooperation with calnexin or calreticulin can be suppressed using a "ERp57 suppressor agent" which, in the context of the present invention, refers to any agent which functions to disrupt or inhibit the ERp57 cooperation with calnexin or calreticulin using any suitable means including calcium depletion, genetic manipulation, calnexin blocking antibodies, and insertion of antisense sequences. An Erp57 suppressor agent may also include agents which inhibit Erp57 activity. Suitable Erp57 suppressor agent also include immunosuppressive agent such as cyclosporin. Suitable ERp57 suppressor agents for specific secretory problems may be selected by any one of several means, including immobilizing ERp57 either by direct linking or by biotinylation and binding to streptavidin to a column and then to use this to interact in vitro with secretory proteins, thereby establishing the binding parameters and any necessary cofactors for the release of proteins. These techniques are described in detail in Harlow, *Antibodies: A Laboratory Manual*, Cold Spring Harbor Laboratory (1988). Alternatively, the changing secretory protein presence due to cooperation of ERp57 with calnexin or calreticulin may be evaluated in the biological preparation by immunoprecipitation of the specific secretory protein before and after the administration of the particular calnexin suppressing agent employed.

In one embodiment of the present invention, the ERp57 suppressor agent acts by calcium depletion in the cytoplasm, or more preferably, in the ER. This can be accomplished using any suitable agent including an ionophore, such as valinomycin or nonactin, or a calcium channel blocker, such as Verapamil, nifedipine or diltiasem.

In another embodiment of the present invention, ERp57 cooperation with calnexin or calreticulin is suppressed by administering to the biological preparation or warm-blooded animal a suitable suppressor of the activity of ERp57. For example, dithiothreitol (dTT) and oxidizing agents.

In another embodiment of the present invention, ERp57 cooperation with calnexin or calreticulin is suppressed by administering to the biological preparation or warm-blooded animal a suitable glycosylation inhibitor, including by way of example, tunicamycin, castanospermine, deoxymannojirimycin, deoxynojirimycin, or swainsonine.

In another aspect of the present invention, ERp57 cooperation with calnexin or calreticulin is suppressed by decreasing the temperature of the biological preparation to about 30° C. For example, the retention of CFTRΔF508, which depends on calnexin for folding and translocation, is temperature sensitive. Reducing the temperature of the cell line to 30° C. allows the CFTRΔF508 channel to get to the plasma membrane, presumably by altering the association with calnexin. This technique is described in detail in Pind, *J. Biol. Chem.*, 269:12784–12788 (1994).

In another aspect of the present invention, the suppression of the cooperation ERp57 with calnexin or calreticulin can be accomplished by treatment of cells with dithiothreitol or diamide to inhibit dissociation of secretory proteins from calnexin. This technique is described in detail in Wada, *J. Biol. Chem.*, 269(10):7464–72 (1994).

An increase of secretory protein production, and hence the success of the method of ERp57 suppressor agent, can be monitored using any one of several techniques, including evaluating the changing secretory protein presence in the biological preparation by immunoprecipitation of the specific secretory protein before and after the administration of the particular calnexin suppressing agent employed. This technique, and other suitable techniques, are described in detail in Harlow, *Antibodies: A Laboratory Manual*, Cold Spring Harbor Laboratory (1988).

Another aspect of the present invention involves a method of treating protein trafficking disorders. Protein trafficking disorders may be treated by suppressing or stimulating the cooperation of ERp57 with calnexin or calreticulin depending upon the etiology of the particular disorder.

For example, a warm-blooded animal suffering from a protein trafficking disorder would benefit from the suppression of the cooperation of ERp57 with calnexin or calreticulin if the disorder is one in which an otherwise biologically active protein is retained in the ER. Such disorders can be identified by an under production of secretory protein recognized by coimmuno-precipitation assays as described in Ou et al., *Nature*, 364:771–776 (1993) and include, by way of example, familial hypercholesterolaemia (class 2 mutations in the LDL receptor), cystic fibrosis (for CFTR, the most common allele in European and North American populations is $\Delta$F508—but 17 is not the only one which affects trafficking) (CFTR$\Delta$F508), Tay-Sachs disease, congenital sucrose isomaltase deficiency, and juvenile pulmonary emphysema.

Secretory proteins which are retained by ERp57 within the ER may aggregate therein or be subject to degradation. These proteins may be identified by coimmunoprecipitation assays as described in Ou et al. *Nature*, 364:771–776 (1993) and include, by way of example, acetylcholine receptor subunits, HMG CoA reductase, calnexin selectively binds mutant proteins, including, by way of example, $\alpha$1-antitrypsin, LDL receptors, $\beta$-hexosaminidase, CFTR and influenza haemagglutinin and, more specifically, the Z mutation as well as the null Hong Kong mutation of $\alpha$1-antitrypsin. The interaction of CFTR and the prolonged association of the $\Delta$F508 mutant protein has been demonstrated and a model is that this association is responsible for the retention of this otherwise functional channel in the ER (Pind, *J. Biol. Chem.*, 269:12784–12788 (1994)).

The cooperation of ERp57 with calnexin or calreticulin can be suppressed by any one of several suitable techniques, including administering a therapeutically effective amount of any one of the calnexin suppressor agents described in detail above. A therapeutically effective amount is determined based on in vitro experiments, followed by in vivo studies.

The ERp57 suppressor agents may be administered by injection, inhalation, infusion, orally, rectally, lingually or transdermally. Depending on the mode of administration, the compounds or separate components can be formulated with the appropriate diluents and carriers to form of ointments, creams, foams, and solutions.

Injection may be intravenous, intramuscular, intracerebral, subcutaneous, or intraperitoneal. For injection or infusion, the compound would be in the form of a solution or suspension. It would be dissolved or suspended in a physiologically compatible solution in a therapeutically effective amount.

For oral administration, the compounds may be in capsule, tablet, oral suspension, or syrup form. The tablets or capsules would contain a suitable amount to comply with the general and preferred ratios set forth below. The capsules would be the usual gelatin capsules and would contain, in addition to the three compounds, a small quantity of magnesium stearate or other excipient.

Tablets would contain the a therapeutically effective amount of the compound and a binder, which may be a gelatin solution, a starch paste in water, polyvinylpyrilidone, polyvinyl alcohol in water or any other suitable binder, with a typical sugar coating.

Syrup would contain a therapeutically effective amount of the compound.

A warm-blooded animal suffering from a protein trafficking disorder which would benefit from stimulation of the cooperation of ERp57 with calnexin or calreticulin can be identified by coimmunoprecipitation as described in detail in Ou et al., *Nature*, 364:771–776 (1993) and include, by way of example, viral cancers and other viral infections. The assembly of functional viral particles requires viral glycoproteins which are processed through the secretory pathway. This has been confirmed with VSV G protein and influenza IIA protein in Hammond et al., *Proc. Natl. Acad. Sci. USA*, 91 (3):913–7 (1994) and in the case of HIV gp120. The HIV gp120 is slowly translocated through the ER because of its long association with the calnexin. ERp57 stimulating agents may prevent the dissociation of HIV gp120, trapping it in the ER.

In order to suppress the production of the viral particles, the cooperation of ERp57 with calnexin or calreticulin can be stimulated by the administration of a therapeutically effective amount of a phosphorylating agent. Suitable phosphorylating agents include: casein kinase II, cdc2 kinase, and protein kinase C. A therapeutically effective amount may be determined based on in vitro experiments, followed by in vivo studies.

Depending on the mode of administration, the ERp57 stimulating agents can be formulated with the appropriate diluents and carriers to form suitable ointments, creams, foams, and solutions as described above. Methods of administration are the same as those outlined above.

The term "treatment" as used within the context of the present invention, refers to reducing or alleviating symptoms in a subject, preventing symptoms form worsening or progressing, inhibition or elimination of the causative agent, or prevention of the infection or disorder in a subject who is free therefrom. Thus, for example, treatment of infection includes destruction of the infecting agent, inhibition of or interference with its growth or maturation, neutralization of its pathological effects and the like. A disorder is "treated" by partially or wholly remedying the deficiency which causes the deficiency or which makes it more severe. An unbalanced state disorder is "treated" by partially or wholly remedying the imbalance which causes the disorder or which makes it more severe.

Within another aspect of the present invention, methods are provided for delivering vector constructs to a warm-blooded animal or biological preparation, wherein the vector construct directs the expression of calnexin, or calnexin lacking in cytosolic or transmembrane domains, thereby acting as a ERp57 suppressor agent or a calnexin stimulating agent.

As utilized within the context of the present invention, "vector construct" refers to an assembly which directs the expression of a gene of interest. The vector construct must include promoter elements, and a sequence which, when transcribed, is operably linked to the gene of interest and acts as a translation initiation sequence. The vector construct may also include a signal which directs polyadenylation, one or more selectable markers, as well as one or more restriction sites.

ERp57 cDNA may be prepared as the gene of interest by obtaining it in full length cloned from mammalian cDNA using any one of several methods described in Sambrook et al., *Molecular Cloning: A Laboratory Handbook*, Cold Springs Harbor Press (1989). In the context of the present invention, the gene of interest is composed of a portion of the gene encoding ERp57 which, when expressed, would disrupt the normal functioning of ERp57, by way of example. Such a vector may serve to disrupt calnexin associations in both or either of its function of translocation and retention. It functions as a ERp57 suppressor agent in any one of several ways, including, by way of example, by introducing vectors containing gene sequences designed to reduce the rate limiting step of association and folding for secretory proteins. Such sequences might include one which is lacking the cytosolic domain. It would as a ERp57 stimulating agent by the introduction of vectors which encode additional ERp57 sequences, thereby increasing the production and decreasing the rate of secretory protein production.

A wide variety of methods may be utilized in order to deliver vector constructs of the present invention to a warm-blooded animal or biological preparation. For example, within one embodiment of the invention, the vector construct is inserted into a retroviral vector, which may then be administered directly into a warm-blooded animal or biological preparation. Representative examples or suitable retroviral vectors and methods are described in more detail in the following U.S. patents and patent applications, all of which are incorporated by reference herein in their entirety: "DNA constructs for retrovirus packaging cell lines", U.S. Pat. No. 4,871,719; "Recombinant Retroviruses with Amphotropic and Ecotropic Host Ranges", PCT Publication No. WO 90/02806; and "Retroviral Packaging Cell Lines and Processes of Using Same", PCT Publication No. WO 89/07150.

Vector constructs may also be carded by a wide variety of other viral vectors, including for example, recombinant vaccinia vectors (U.S. Pat. Nos. 4,603,112 and 4,769,330), recombinant pox virus vectors (PCT Publication No. WO 89/01973), poliovirus (Evans et al. *Nature*, 339:385–388 (1989); and Sabin, *J. Biol. Standardization*, 1:115–118 (1973)); influenza virus (Luytjes et al., *Cell*, 59:1107–1113 (1989); McMichael et al., *N. Eng. J. Med.*, 309:13–17 (1983); and Yap et al., *Nature*, 273:238–239 (1978)); adenovirus (Berkner, *Biotechniques*, 6:616–627 (1988); Rosenfeld et al., *Science*, 252:431–34 (1991)); adeno-associated virus (Samulski et al., *J. Vir.*, 63:3822–3828 (1989); Mendelson et al., *Virol.*, 166:154–165 (1988)); herpes (Kit, *Avd. Exp. Med. Biol.*, 215:219–236 (1989)); and HIV (Poznansky, *J. Virol.*, 65:532–536 (1991)).

In addition, vector constructs may be administered to warm-blooded animals or biological preparations utilizing a variety of physical methods, such as lipofection (Felgner et al. *Proc. Natl. Acad. Sic. USA*, 84:7413–7417 (1989), direct DNA injection (Acsadi et al., *Nature*, 352:815–818 (1991)); microprojectile bombardment (Williams et al., *PNAS*, 882726–2730 (1991)); liposomes (Wang et al., *PNAS*, 84:7851–7855 (1987)); CaPO4 (Dubensky et al., *PNAS*, 81:7529–7533 (1984)); or DNA ligand (Wu et al., *J. Biol. Chem.*, 264:16985–16987 (1989)).

A therapeutic amount may be determined by in vitro experimentation followed by in vivo studies.

Yet another aspect of the present invention concerns a method of treating protein trafficking disorders by targeting a suitable ERp57 suppressor agent, ERp57 stimulating agent, or any other agent designed to interfere with cooperation of ERp57 with calnexin or calreticulin. For the purposes of illustrating this aspect of the invention, "targeting moiety" refers to any polypeptide molecule from a dipeptide up to, and including, any protein or protein containing compound or any functional equivalent, including those without an amino acid basis, that binds to a desired target site. In a preferred embodiment of the present invention, this method is utilized to deliver calcium depletion agents directly to the ER.

Suitable targeting moieties include any moiety which specifically binds to a cell surface receptor preferably an ER membrane receptor and is capable of affecting the protein trafficking pathway. Suitable targeting moieties include proteins, peptides, and non-proteinaceous molecules. Representative examples of suitable targeting moieties include antibody and antibody fragments; peptides such as bombesin, gastrin-releasing peptide, cell adhesion peptides, substance P, neuromedin-B, neuromedin-C and metenkephalin; hormones, including EGF, alpha- and beta-TGF, estradiol, neurotensin, melanocyte stimulating hormone, follicle stimulating hormone, luteinizing hormone, and human growth hormone; proteins corresponding to ligands for known cell surface receptors, including low density lipoproteins, transferrin and insulin; fibrinolytic enzymes; and biological response modifiers, including interleukin, interferon, erythropoietin and colony stimulating factor also constitute targeting moieties of this invention. Moreover, analogs of the above targeting moieties that retain the ability to specifically bind to a cell surface receptor, preferably an ER membrane receptor, are suitable targeting moieties. Essentially any analog having about the same affinity as a target moiety, herein specified, could be used in synthesis of receptor modulators.

In a preferred embodiment, the targeting moiety is an antibody or antibody fragment. Particularly preferred antibodies include monoclonal antibodies having high specificity for an ER membrane receptor and the ability to catalyze the internalization of the conjugate. Suitable antibodies may be selected by assays for internalization known in the art and described in detail in *Cancer Treat. Res.*, 68:23 (1993); *Leuk. Lymp.*, 9:293 (1993); *Anticancer Drub Des.*, 7:427 (1992) (incorporated herein by reference). All anti-calnexin antibody can be produced by methods well known in the art and described in Harlow et al, *Antibodies: A Laboratory Manual*, Cold Spring Harbor Laboratory (1988), incorporated herein by reference. The immunoconjugate comprises at least one agent coupled to an anti-ERp57 antibody. A single or multiple molecules of one type of agent may be coupled to an antibody. Alternatively, more than one type of agent may be coupled to an antibody.

The basic requirement of the targeting moiety is that the polypeptide increases the specificity of the therapeutic agent toward the desired site, either in or in vitro, depending on the application. Thus, the targeting polypeptides can include proteins having certain biological activities rendering them specific for desired sites.

Suitable targeting polypeptides include but are not limited to receptors, hormones, lymphokines, growth factors, substrates, particularly compounds binding to surface membrane receptors. Suitable receptors include surface membrane receptors, antibodies, enzymes, naturally occurring receptors, lectins, and the like. Of particular interest are immunoglobulins or their equivalents.

The targeting moiety may be readily labeled or conjugated to a wide variety or molecules, including for example, toxins, fluorescent molecules, magnetic resonance enhancers, or radionuclides. Representative examples of toxins include ricin, abrin, diphtheria toxin, cholera toxin, gelonin, pokeweed antiviral protein, tritin, Shigella toxin, and Pseudomonas exotoxin A. Representative examples of fluorescent molecules include fluorescein, phycoerythrin, rhodamine, Texas red and luciferase. Representative examples of radionuclides include Cu-64, Ga-67, Ga-68, Zs-89, Ru-97, Tc-99m, Rh-105, Pd-109, In-111, I-123, I-125, I-131, Re-186, Re-188, Au-198, Au-199, Pb-203, At-211, Pb-212 and Bi-212. Methods for labeling or conjugating the targeting moiety to any of the above described compounds or compositions may be readily accomplished by one of ordinary skill in the art given the disclosure provided herein (see also Trichothecene Antibody Conjugate, U.S. Pat. No. 4,744,981; Antibody Conjugate, U.S. Pat. No. 5,196,951; fluorogenic Materials and Labeling Techniques, U.S. Pat. No. 4,018,884; Metal Radionuclide Labeled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, *Methods in Enzymology*, Vol. 34, Affinity *Techniques, Enzyme Purification*: Part B, Jakoby and Wichek (eds.), Academic Press, New York, P. 30, (1974); see also Wilehek and Bayer, "The Avidin-Biotin Complex in Bioanalytical Applications", *Anal. Biochem.,* 171:1–32 (1988)).

A ERp57 suppressor or stimulating agent may be coupled to, i.e., covalently bonded to, the targeting moiety either directly or via a linker group. It will be evident to those of ordinary skill in the art that a variety of bifunctional reagents may be employed as the linker group. A preferred method is described in U.S. Pat. No. 5,094,848 (the '848 patent), incorporated herein by reference. Briefly, the '848 patent discloses a method of binding a therapeutic agent by a cleavable diphosphate or amidated diphosphate linkage to a protein specific for the targeting site, guiding the therapeutic agent directly to the targeted site. The conjugate so created possesses the ability to selectively deliver one or more agents to the ER.

The conjugate is administered in a therapeutically effective amount in a suitable excipient. The effective amount for a particular conjugate may be determined based on in vitro experiments followed by in vivo studies. Depending on the mode of administration, the complex can be formulated with the appropriate diluents and carriers to form ointments, creams, foams, and solutions. Methods of administration are identical to those outlined above.

In another aspect of the present invention, the a targeting moiety conjugated to a reporting group may be used to detect protein trafficking disorders. By administering a ward-blooded animal or a biological preparation and effective amount of such a conjugate, wherein the agent is a reporter group, such as a radionuclide or magnetic resonance enhancer, and detecting the level of the reporter group, the level of calnexin activity can be ascertained.

The effective amount of conjugate necessary may be determined based upon in vitro experiments, followed by in vivo studies. The step of detecting a radionuclide is typically performed with an imaging carriers using a detector appropriate for the particular radionuclides type of emission. These techniques are described in detail in Harlow et al., *Antibodies: A Laboratory Manual* Cold Spring Harbor Laboratory (1988), incorporated herein by reference. The step of detecting a magnetic resonance imaging enhancer is likewise well known in the art.

By detecting the levels of ERp57 in the warm-blooded animals or biological preparation using these well-known techniques and the disclosure herein, those of ordinary skill in the art will be able to gauge calnexin levels and identify protein trafficking disorders or the risk thereof.

In another aspect of the present invention, the ERp57 suppressor agent can be administered in combination with calnexin suppressor agent. Calnexin suppressor agents are described in U.S. Pat. No. 5,691,306 of which the content is incorporated by reference.

In another aspect of the present invention, the ERp57 stimulator agents can be administered in combination with a calnexin stimulator agent. Calnexin stimulator agents are described in U.S. Pat. No. 5,691,306 of which the content is incorporated by reference.

PDI has been studied for 35 years and its activity seemed sufficient to account for the rapid formation of disulfide bonds in the ER. Indeed, an amount of PDI equivalent to that found in an ER extract produced similar in vitro refolding rates of bovine pancreatic trypsin inhibitor as the total extract (Zapun et al., (1997) *Cell,* 88:29–38). Other thiol-disulfide oxidoreductases similar in sequence to PDI were later also found in the ER, but their functions have remained elusive. Currently, five additional PDI-like proteins have been identified in mammals: ERp57, ERp72, P5 (reviewed in ref. (Freedman et al., (1994) *Trends Biochem Sci.,* 19:331–336)), PDIR (Hayano et al., (1995) *FEBS Lett.,* 372:210–214), and PDIp which is specific to the pancreas (Desilva et al., (1996) *DNA Cell Biol.,* 15:9–16). That ERp57 could be cross-linked to the same substrates as calnexin and calreticulin was the first indication that the various PDI-like proteins might be dedicated to different classes of proteins (Oliver et al., (1997) *Science,* 275:86–88).

PDI catalyzes the rearrangement of disulfide bonds, even if they are buried and stabilized by the native structure of the substrate, as for example with some folding intermediates of the bovine pancreatic trypsin inhibitor. The isolated a and a' thioredoxin domains of PDI have no isomerase activity, although they retain their oxidoreductase activity (Darby et al., (1995) *Biochemistry,* 34:11725–11735). The isomerase activity may result from protein-protein interactions between PDI and its substrates in addition to the catalysis of thiol-disulfide interchange (Kemmink et al., (1997) *Curr. Biol.,* 7:239–245). That PDI binds unfolded proteins is supported by the chaperone activity which PDI exhibits (Puig et al., (1994) *J. Biol. Chem.,* 269:7764–7771) even on a protein without disulfide bonds (Cai et al., (1994) *J. Biol. Chem.,* 269:24550–24552), and which can be separated from the oxidoreductase activity by alkylating the active site cysteines (Quan et al., (1995) *J. Biol. Chem.,* 270:17078–17080). When substrates are bound to calnexin or calreticulin, their binding to PDI may be restricted, thus impeding the isomerase activity. Either ERp57 has a conformation which avoids this problem of steric hinderance, or the role of handling the substrate is played entirely by the lectins.

Other characteristics and advantages of the present invention will appear from the following examples. The following examples are intended to document the invention, without limiting its scope.

EXAMPLE 1

Enhanced Catalysis of Ribonuclease B Folding by the Interaction of Calnexin or Calreticulin with ERp57 Proteins Human ERp57 was produced in Escherichia coli (BL21 (DE3), pLysS) with a pET9 vector (Studier et al., (1990)

Methods Enzymol., 185:60–89). The construct encoded the protein without a signal sequence (residue 25–505) (Koivunen et al., (1996) Biochem J., 316:599–605) but with an additional alanine residue at the N-terminus. The soluble cell extract was loaded onto a heparin SEPHAROSE column equilibrated with 10 mM Tris-HCl (pH 7.4). Proteins were eluted stepwise with 200 and 600 mM NaCl in the same buffer. The 600 mM NaCl fraction was dialyzed against 10 mM Tris-HCl (pH 7.4) and ERp57 was further purified on a Q-SEPHAROSE column eluted with a gradient of 0–400 mM NaCl in the same buffer. Rabbit antiserum was generated against the purified protein. Human PDI, calnexin ΔTMC and calreticulin were prepared as described previously (Darby et al., (1995) Biochemistry, 34:11725–11735, Ou et al., (1993) Nature, 364:771–776 and Baksh et al., (1992) Protein Expr. Purif., 3:322–331). The cDNA of UGGT from Drosophila melanogaster was expressed in Sf9 insect cells with a baculovirus vector. The signal sequence was replaced with that of melittin (Tessier et al., (1991) Gene, 98:177–183) and the ER retention sequence HGEL was changed for six histidines (Tessier et al., unpublished) . The protein was purified from the culture medium on a Ni-NTA agarose column (Qiagen). Affinity chromatography purified RNase B was from Sigma. Denaturation of RNase B and glucosylation with UDP-[3H]glucose were performed as previously described (Zapun et al., (1997) Cell, 88:29–38).

Refolding of RNase B

After glucosylation, refolding was initiated by dissolving freeze-dried reduced RNase B (~60 μM) in 20 mM Tris-HCl (pH 7.5), 150 mM NaCl, 2 mM CaCl2, 0.5 mM oxidized glutathione, 2 mM reduced glutathione, with or without 18 12 μM of ΔTMC or calreticulin, and 18 4 μM of either ERp57 or PDI, at 25° C. Aliquots were withdrawn after various times, reacted for 5 minutes at room temperature with 0.25 volumes of 0.5 M iodoacetamide in 1.5 M Tris-HCl (pH 8.7), and then stored on ice prior to analysis by low pH non-denaturing PAGE (Creighton, T. E., (1979) J. Mol. Biol., 129:411–431). The incorporation of [3H] glucose was detected by fluorography (Amplify, Amersham).

Oligosaccharide-ERp57-Binding

After monoglucosylation, oligosaccharides were released by incubation of 1.2 mg/ml of RNase B with 0.1 U/ml of Endo H (Boehringer Mannheim) for 3 h at 37° C. in 20 mM Tris-HCl (pH 7.5), 150 mM NaCl and 2 mM CaCl2. A fraction of the mixture containing 60 μg of Rnase B was then incubated for 15 minutes at room temperature with either of 18 1.6 μM of ΔΔTMC or 18 3 μM of ERp57 in 0.5 ml of the same buffer. Samples were then separated by gel filtration as described previously (Zapun et al., (1997) Cell, 88:29–38). Radiolabelled G1-oligosaccharides in the collected fractions were determined by liquid scintillation counting. To check the binding of the whole glycoprotein, RNase B after monoglucosylation was mixed directly with ΔTMC or ERp57. Analysis by gel filtration and SDS-PAGE was as described previously (Zapun et al., (1997) Cell, 88:2938–38).

ERp57-ΔTMC Binding

ERp57 (18 0.5 μg) was incubated for 5 minutes at room temperature with 40 μg of ΔTMC or ~80 μg of catalase in 0.5 ml of 20 mM Tris-HCl (pH 7.5), 150 mM NaCl and 2 mM CaCl2. The mixture was separated by gel filtration as above. The proteins in collected fractions were precipitated with 10% trichloroacetic acid prior to analysis by reducing SDS-PAGE. The presence of ERp57 was revealed by immunoblotting developed with ECL (Amersham).

Refolding of RNase B in the Presence of Calnexin or Calreticulin and ERp57

To demonstrate the function of ERp57, its disulfide isomerase activity on the refolding of G1-RNase B was examined. RNase B has the same sequence as RNase A, but is glycosylated on residue Asn34. RNase A and B both contain eight cysteine residues which form four disulfide bonds that are required for the native structure, and the proteins unfold upon reduction of these bonds. The disulfide-coupled refolding of RNase A and of RNase B have been well characterized and are similar (Creighton, T. E. (1979) J. Mol. Biol., 129:411–431 and, Grafl et al., (1987) J. Biol. Chem., 262:10624–10629). Unfolded reduced RNase B is a substrate for UGGT (Zapun et al., (1997) Cell, 88:29–38) and the monoglucosylation was performed with UDP-[3H]glucose. Due to the heterogeneity of the glycans of RNase B, the glucosylation reaction is rather inefficient (~1%) (Zapun et al., (1997) Cell, 88:29–38). When examined by gel electrophoresis, the small fraction of G1-RNase B was only detectable by autoradiography (AR), whereas the large excess of nonmonoglucosylated RNase B was observed by Coomassie blue staining (CB), providing a useful internal control (Zapun et al., (1997) Cell, 88:29–38).

Figures 1A, 1B:
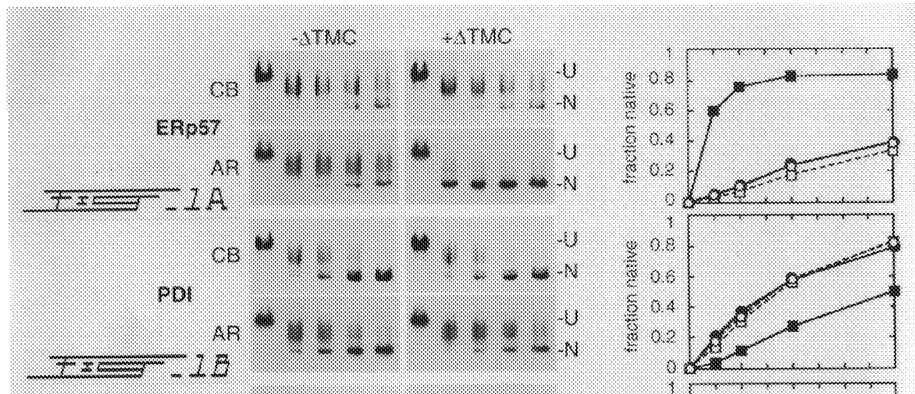
FIG. 1 illustrates the refolding of RNase B catalyzed by ERp57 or PDI, with or without calnexin After monoglucosylation, refolding of reduced Rnase B was initiated in a gluthatione redox buffer in the presence of Erp57 (a) or PDI (b) or without catalyst (CTL, c) and in the absence or the presence of the lumenal domain of calnexin

Refolding was initiated by dissolving the reduced RNase B in a glutathione buffer which approximates the redox conditions of the ER (Hwang et al., (1992) Science, 257:1496–1502). The influence of calnexin was tested by adding a soluble recombinant form (residues 1–462) which lacks the transmembrane and cytoplasmic segments (ΔTMC) (Ou et al., (1995) J. Biol. Chem., 270:18051–18059). The refolding reaction was terminated at various times by alkylation of the free thiols with iodoacetamide and the conformation of RNase B was determined by non-denaturing PAGE. In the presence of ERp57, the rate of appearance of native RNase B was markedly increased (FIG. 1, compare panels A and C). In the absence of calnexin (FIG. 1A, -ΔTMC), no difference was observed in the folding rate between G1-(AR) and non-G1-RNase B (CB). When calnexin was included, the rate of disulfide rearrangement of G1-RNase B was greatly increased (FIG. 1A, +ΔTMC, AR), whereas the refolding rate of the bulk of the RNase B molecules remained unaffected (FIG. 1A, +ΔTMC, CB). The same effect was observed when calreticulin was added instead of calnexin (data not shown).

Figure 1C:
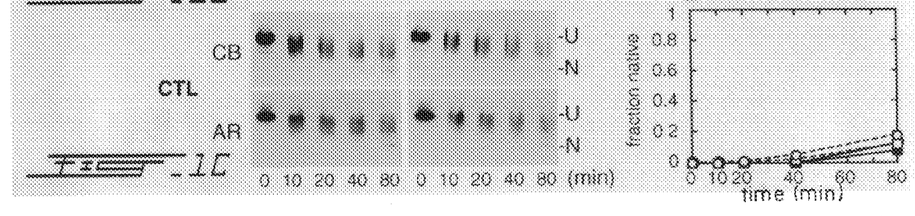

This result with ERp57 is in marked contrast to that observed with PDI. In the absence of calnexin, PDI exhibited a greater disulfide isomerase activity than ERp57 (FIG. 1, -ΔTMC, compare panels B and A). The monoglucosylation of RNase B (AR) did not influence the activity of PDI. The presence of calnexin did not influence the isomerization of the disulfide bonds in the non-G1-RNase B (FIG. 1B, +ΔTMC, CB). However, calnexin did inhibit the catalysis of the refolding of G1-RNase B (FIG. 1B, -ΔTMC, AR). This effect of calnexin on the activity of PDI, which was previously reported (Zapun et al., (1997) Cell, 88:29–38), is the opposite of its effect on ERp57. Calreticulin had the same effects (data not shown). In the absence of either catalyst, the refolding of RNase B was very slow and no effect of calnexin could be reliably measured (FIG. 1C). These results demonstrate that binding of G1-RNase B to calnexin or calreticulin favors the catalysis of disulfide bond rearrangement by ERp57, whereas it hampers catalysis by PDI.

Absence of binding of G1-glycans to ERp57

Figure 2A:
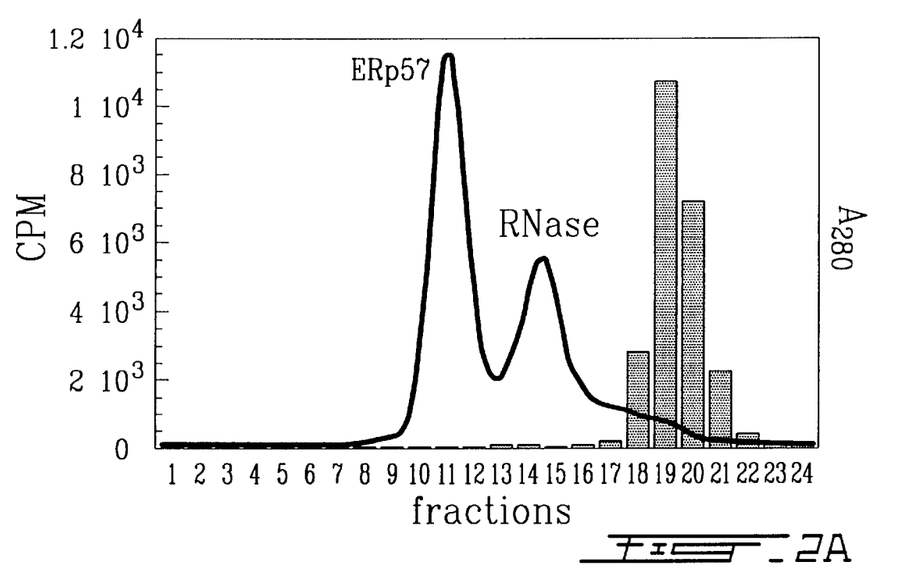
FIG. 2 illustrates the interaction between Erp57 or calnexin with and calnexin After monoglucosylation of RNase B, the oligosaccharides were released with Endo H. After incubation with (a) ERp57 or (b) ΔTMC, the mixtures were separated by gel filtration. Proteins were monitored at 280 nm (solid line), and radiolabeled G1-oligosaccharides in collected fractions were detected by liquid scintillation counting (columns). (c) a small amount of ERp57 was incubated with a large excess of ΔTMC or catalase prior to separation by gel filtration. ERp57 in collected fractions was revealed by Western blotting. The peak of ERp57 detected at 280 nm is from a separate experiment with a much greater amount of protein
Figure 2B:
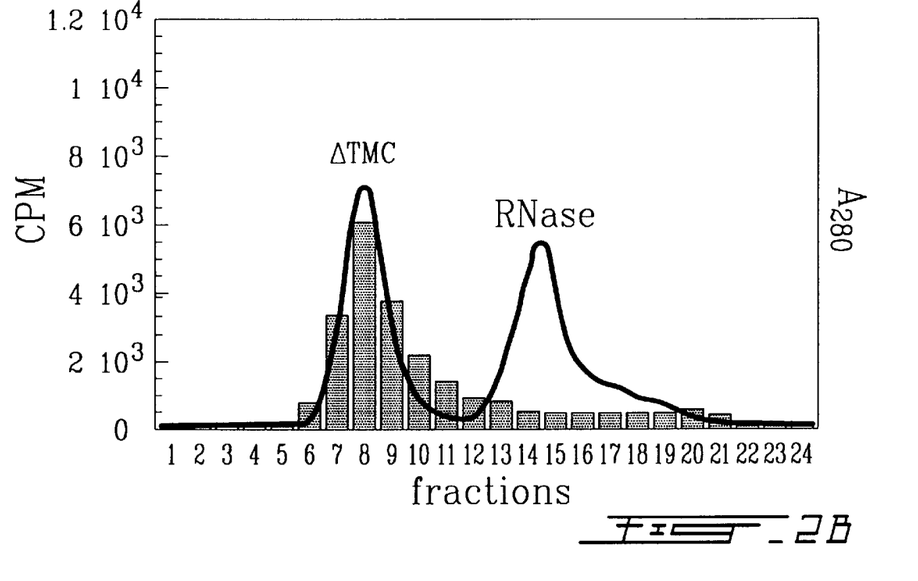
Figure 3:
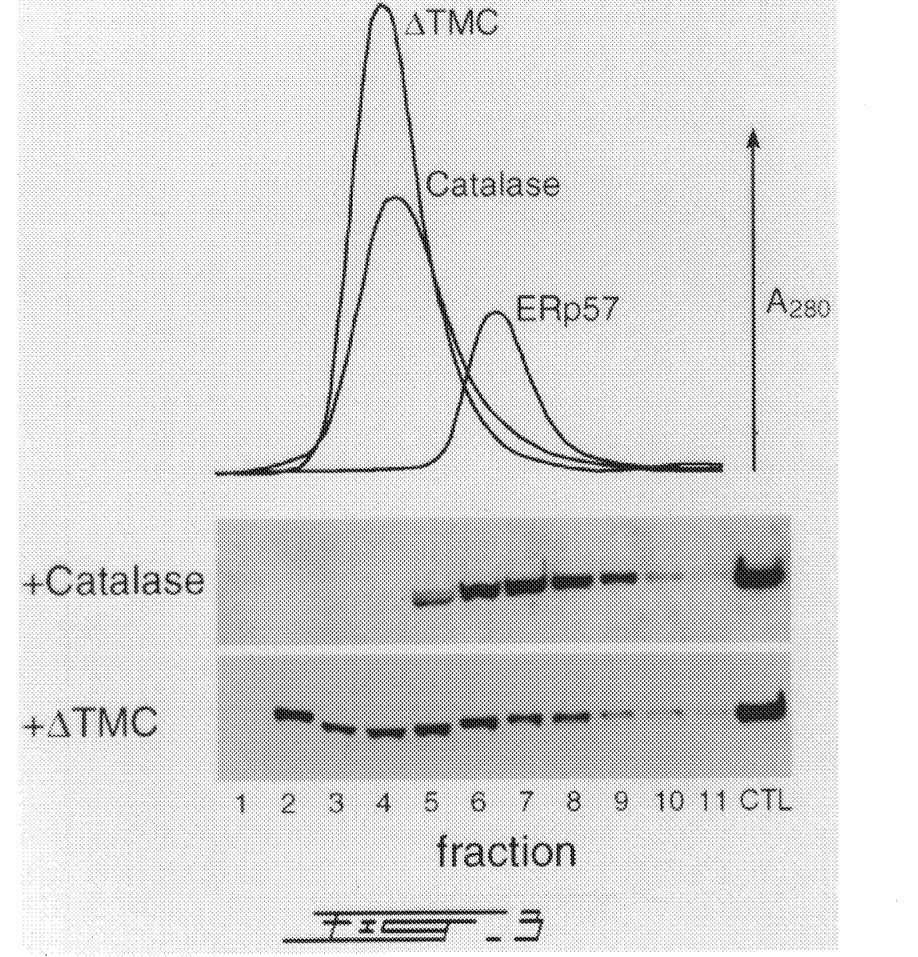
FIG. 3 illustrates the binding of ERp57 to calnexin.

The catalysis by ERp57 in the absence of calnexin is independent of monoglucosylation suggesting that ERp57 does not recognize the glycan of the substrate. It was determined if ERp57 directly binds G1-oligosaccharides or G1-RNase B. After monoglucosylation, glycans were released from RNase B by treatment with endo-β-N-acetylglucosaminidase H (Endo H). The EndoH-treated protein was mixed with ERp57 or calnexin. After separation by gel filtration (Zapun et al., (1997) Cell, 88:29–38), the radioactivity was counted in collected fractions. No binding of G1-oligosaccharide (FIG. 2A and 2B) or of G1-RNase B (data not shown) to ERp57 could be detected. Association of ERp57 and Calnexin To examine whether there is a direct interaction between calnexin and ERp57, advantage was taken of the large apparent molecular weight of ΔTMC which allowed its separation from ERp57 gel filtration. Thus, a small amount of ERp57 was mixed with and excess of ΔTMC and examined by size exclusion Chromatography. After precipitation, the proteins in the collected fractions were analyzed by SDS-PAGE. The presence of ERp57 was revealed by immunoblotting (FIG. 2C). In the presence of calnexin, the elution peak of RERp57 was shifted to earlier fractions coinciding with the calnexin peak. In a control experiment with catalase instead of calnexin, as they have similar elution times, the elution of ERp57 was not altered. This demonstrates that ERp57 binds to calnexin even in the absence of substrate. This binding is not due to the glycosylation of ERp57 as its sequence does not predict a glycosylation sequon and also the protein used int his study was expressed in Escherichia coli. Thus, the interaction between calnexin and ERp57 is specific protein-protein contact, which is different from the lectin-type binding of G1-glycoproteins to calnexin.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. A method for folding unfolded proteins or for enhancing the formation of folded proteins which comprises a step of exposing an unfolded protein to a biological preparation comprising an ERp57 specifically bound to calnexin or calreticulin under conditions to permit folding of the unfolded protein.

2. A method for forming disulfide bonds in an unfolded protein or for enhancing the formation of disulfide bonds in an unfolded protein which comprises a step of exposing an unfolded protein to a biological preparation comprising an ERp57 specifically bound to calnexin or calreticulin under conditions to permit folding of the unfolded protein.

3. The method of claim 1 wherein said unfolded protein is a secretory protein.

4. The method of claim 2 wherein said unfolded protein is a secretory protein.

* * * * *

UNITED STATES PATENT AND TRADEMARK OFFICE
CERTIFICATE OF CORRECTION

PATENT NO.    : 6,476,194 B1
DATED         : November 5, 2002
INVENTOR(S)   : Daniel C. Tessier et al.

It is certified that error appears in the above-identified patent and that said Letters Patent is hereby corrected as shown below:

<u>Title page,</u>
Item [75], second inventor's name should read -- André Zapun --

<u>Column 13,</u>
Line 32, "18 12µM" should read -- ~ 12µM --
Line 33, "18 4µM" should read -- ~ 4µM --
Line 49, "18 1.6µM of ΔΔTMC" should read -- ~ 1.6µM of ΔTMC --
Line 49, "18 3µM" should read -- ~ 3µM --
Line 60, "18 0.5µg" should read -- ~ 0.5µg --

Signed and Sealed this

Third Day of June, 2003

JAMES E. ROGAN
*Director of the United States Patent and Trademark Office*